(12) United States Patent
Kim et al.

(10) Patent No.: US 6,703,501 B1
(45) Date of Patent: Mar. 9, 2004

(54) LAYERED SILICATE CATALYSTS PILLARED WITH METAL OXIDE

(75) Inventors: Myunghun Kim, Seoul (KR); Sunjin Kim, Seoul (KR); Youngsun Uh, Kyonggi-Do (KR); Younghee Kim, Seoul (KR)

(73) Assignee: Korea Institute of Science and Technology (KR)

( * ) Notice: Subject to any disclaimer, the term of this patent is extended or adjusted under 35 U.S.C. 154(b) by 0 days.

(21) Appl. No.: 10/088,785

(22) PCT Filed: May 26, 2000

(86) PCT No.: PCT/KR00/00542

§ 371 (c)(1),
(2), (4) Date: Jun. 11, 2002

(87) PCT Pub. No.: WO01/21305

PCT Pub. Date: Mar. 29, 2001

(30) Foreign Application Priority Data

Sep. 21, 1999 (KR) .................................... 1999/40680

(51) Int. Cl.[7] ............................................... B01J 23/20
(52) U.S. Cl. ................................................... 540/536
(58) Field of Search ........................................ 540/536

(56) References Cited

U.S. PATENT DOCUMENTS

| | | | |
|---|---|---|---|
| 4,709,024 A | 11/1987 | Sato et al. | 540/536 |
| 4,717,769 A | 1/1988 | Sato et al. | 540/536 |
| 4,717,770 A | 1/1988 | Sato et al. | 540/536 |
| 4,812,222 A | 3/1989 | Kirker et al. | 208/89 |

FOREIGN PATENT DOCUMENTS

| | | |
|---|---|---|
| DE | 10920 | 9/1880 |
| EP | 0242960 | 10/1987 |
| EP | 0508005 | 10/1992 |
| EP | 0509493 | 10/1992 |
| GB | 881276 | 11/1961 |
| GB | 881927 | 11/1961 |
| JP | 57139062 | 8/1982 |
| JP | 271669 | 10/1993 |
| JP | 7126058 | 5/1995 |

OTHER PUBLICATIONS

"Organic Reactions Catalyzed by Crystalline Aluminosilicates", Journal of Catalyst, vol. 6, p. 247; 1966.

*Primary Examiner*—Bruck Kifle
(74) *Attorney, Agent, or Firm*—Ostrolenk, Faber, Gerb & Soffen, LLP

(57) ABSTRACT

The present invention relates to porous catalysts comprising layered silicate and metal oxides, and a method of preparing ε-caprolactam from cyclohexanone oxime using the catalyst. This new catalyst can resolve the environmental and safety problems arising from conventional liquid acid process. Also the present catalyst solves the problem of short lifetime of current solid acid catalysts. Moreover, the present catalyst provides higher selectivity and yield.

12 Claims, No Drawings

LAYERED SILICATE CATALYSTS PILLARED WITH METAL OXIDE

TECHNICAL FIELD AND BACKGROUND ART

The present invention relates to a porous catalyst with controlled pore sizes comprising layered silicates and metal oxides and a preparation method thereof. The present invention also relates to a method for preparing $\epsilon$-caprolactam using-the porous catalyst in a vapor phase.

The manufacture of $\epsilon$-caprolactam from cyclohexanone oxime via Beckmann rearrangement reaction is an industrially important process. $\epsilon$-Caprolactam is used as a raw material for nylon-6 synthesis. The commercial process for producing $\epsilon$-caprolactam is now being carried out in a liquid phase using a fuming sulfuric acid as a catalyst. In such a process, it is necessary to neutralize the sulfuric acid with ammonia in order to separate the produced is lactam, whereby ammonium sulfate is produced as by-products of 2–3 tons per 1 ton of the $\epsilon$-caprolactam produced. Thus, the recovery and disposal of the by-products add substantial and extra cost to the production of $\epsilon$-caprolactam. In addition, the sulfuric acid causes corrosion of the reaction vessel, whereby safety and environmental problems in treating concentrated sulfuric acid are also posed.

To resolve these problems, various studies have been made to develop solid acid catalysts for the Beckmann rearrangement reaction in a vapor phase since mid of 1960's. For example, boric acid (German Patent No. 10920), silica-alumina (UK Patent No. 881,927), phosphoric acid (UK Patent No. 881,276), zeolites (Journal of Catalyst, Vol. 6, p 247, 1966), tantalum oxide supported on silica (European Patent Publication No. 509,493 A1) have been proposed as solid acid catalysts for the Beckmann rearrangement reaction of cyclohexanone oxime.

European Patent Publication No. 509,493 A1 discloses a method for preparing $\epsilon$-caprolactam, which comprises subjecting cyclohexanone oxime to a Beckmann rearrangement reaction in a vapor phase in the presence of tantalum oxide supported on silica, wherein the catalyst is prepared by contacting tantalum ailkoxide to a ammorphous silica. ($Ta_2O_5$ 1–30 wt % /$SiO_2$) In these cases, the pore structure of silica carriers was important for the catalytic performance. The high ratio (>90%) of the pore volume for fine pores with diameters from 40 to 2,000 Å to total pore volume (40 to 150,000Å) of silica carriers was effective.

Japanese published unexamined patent application No.139062/1982 discloses crystalline alumino-silicates e.g. ZSM-5 having 40–60 of Si/Al atomic ratio show low selectivity of $\epsilon$-caprolactam although conversion of cyclohexanone oxime is said to be nearly complete. Whereas U.S. Pat. No. 4,709,024 discloses the catalytic activity of ZSM-5 improves with the increase in the Si/Al ratio to 500. These studies indicate that high Si/Al ratio in MFI zeolites give an improved catalytic performance for the Beckmann rearrangement of cyclohexanone oxime.

U.S. Pat. No. 4,717,769 further discloses the production of $\epsilon$-caprolactam by a vapor-phase catalytic rearrangement of the cyclohexanone oxime in the presence of crystalline metallo-silicates. These include Ga, Fe, B, Zr, Bi, Nb, Zn, Be, Cr, La, Ti, Hf, V and/or Cu substituted forms in high Si/Al ratio of MFI zeolites. Although the improved solid acid catalysts show a high conversion for the cyclohexanone oxime and selectivity for the caprolactam at initial stage, the catalytic activities do not last for a long period. To replace homogeneous process with vapor phase process in the industrial mass production of $\epsilon$-caprolactam, the solid acid catalyst must have an improved catalytic activity and it's lifetime;

According to the many studies reported, the solid acid catalyst should have weak acidic hydroxyl groups attached preferably on the surface of the solid acid catalysts for Beckmann the rearrangement of cyclohexanone oxime. It is suggestive that an efficient solid acid catalyst for the rearrangement of cyclohexanone oxime can be achieved if the catalyst possesses abundant hydroxyl groups having weak acidity. Layered silicates, such as kanemite ($NaHSi_2O_5 3H_2O$), magadiite ($Na_2Si_{14}O_{29} 11H_2O$), kenyaite ($K_2Si_{20}O_4 11H_2O$) makatite ($Na_2Si_4O_9 5H_2O$) and ilerite ($Na_2Si_8O_{17} xH_2O$) are composed of tetrahedral silicate sheets only and the each silicate sheet terminates with the hydroxyl groups. The layered silicates, therefore, possess abundant hydroxyl groups, and have a great potential to act as new catalysts for the vapor phase Beckmann rearrangement reaction.

In the present invention, an efficient solid acid catalyst for the vapor phase Beckmann rearrangement reaction is designed using layered silicates Small amount of metal oxide was intercalated between the silicate layers by usual pillaring process to generate moderate acidity as a mixed oxide and to increase thermal stability of layered silicates for use in catalysis.

SUMMARY OF THE INVENTION

The present invention provides a new porous catalyst for preparing $\epsilon$-caprolactam comprising layered silicates and metal oxides to solve the problems occurred in the conventional techniques.

Another object of the present invention is to provide a method for preparing the porous catalyst, wherein the method comprises the steps of substituting $Na^+$ ion of the layered silicate with $H^+$ ion in an inorganic acid solution, expanding the interlayer distance between the silicate layers to 20–30 Å using a long chain amine, inserting metal oxide in the above silicate layers and calcinating the resultant product.

DETAILED DESCRIPTION OF THE INVENTION

The present invention relates to a porous catalyst comprising layered silicates and metal oxides whose pore sizes are controlled, a method for preparing the porous catalyst, and a method for preparing $\epsilon$-Caprolactam from cyclohexanone oxime using the porous catalyst in a vapor phase.

The present inventors have succeeded in preparing weak solid acid catalyst by pillaring metal oxides to layered silicate that possesses abundant hydroxyl groups. The inventors also succeeded in using this solid acid catalyst as a catalyst for a Beckmann rearrangement of cyclohexanone oxime. The catalyst of the present invention has a higher conversion for cyclohexanone oxime, a high selectivity for $\epsilon$-caprolactam and a long life time when compared to the zeolite catalyst having MFI structure with a high silicate composition.

The present invention provides a layered silicate catalyst pillared with metal oxide and a method for preparing the same. More particularly, the porous catalyst of the present invention comprises layered silicates and metal oxides. The metal oxides are pillared between the silicate layers in the present invention. The method for preparing a porous catalyst comprises the steps of substituting $Na^+$ ion of the layered silicate with H⁺ ion in an inorganic acid solution, expanding the interlayer distance between the silicate to 20–30 Å using a long chain amine such as octylamine, inserting metal oxides between the silicate layers and calcinating the resultant product. The method for pillaring metal oxide between the layered materials is generally well known. However, it has not been used as catalyst for the Beckmann rearrangement of cyclohexanone oxime prior to the present invention.

In the present specification, "pillaring of metal oxides between silicate layers" means that metal oxides are inserted between silicate layers like rods such a manner that the pillared metal oxide is bonded to the two layers and thus the structure of the layered silicates is maintained Layered silicates have a two-dimensional structure, and abundantly exist in the nature. Thus, the layered silicates are commercially available or some of the layered silicates can be easily synthesized in the laboratory. Unlike clays, the layered silicates comprise only tetrahedra of $SiO_4$ and cation such as $Na^+$. The structure of the layered silicates is maintained through weak electrostatic interactions between the negatively charged silicate layers and positively charged $Na^+$ ion. The $Na^+$ ion can be easily substituted with other ions through an ion exchange method. For instance, $Na^+$ ions between the layers can be easily exchanged with $H^+$ ions in inorganic acid solutions such as hydrochloric acid or sulfuric acid. Small amount of metal oxide was intercalated between the silicate layers by usual pillaring process to generate moderate acidity as a mixed oxide and increase the thermal stability of the layered material for use in catalysis. Silica layers pillared with metal oxide have a superior property as a solid acid catalyst. It has been reported that the layered silicates pillared with metal oxides such as Cr, Mo, W, Fe, Co and Ni were used as catalysts for hydrocarbon cracking reaction (EP 508005, JP 05-271669).

In the layered silicate catalysts of the present invention, metal oxide can be pillared between the layered silicates in the amount of 0.5–30 weight %, preferably, 2–10 weight %. The interlayer distance between the silicate layers is 5 to 30 Å, preferably 5 to 15 Å, and the surface area of the prepared catalyst is 100–500 m²/g, preferably 100–300 m²/g.

The layered silicate materials that can be used in the present invention include kanemite, magadiite, kenyaite, makatite, ilerite, and octosilicate. Some of these can be easily synthesized in the laboratory.

The catalyst of the present invention can be prepared by pillaring a variety of metal oxides such as $Ta_2O_5$, $Nb_2O_5$, $TiO_2$, or $SiO_2$ between the silicate layers. The catalyst have internal pores of about 5 to 30 Å in diameter.

When the layered slicate catalyst pillared with metal oxide used in Beckmann rearrangement of cyclohexanone oxime the catalytic activity at the initial stage of the reaction is high; the conversion of cyclohexanone oxime is 97% and the selectivity for caprolactam is 95%. In addition, the catalyst of the present invention shows high conversion and selectivity for a long period of time and is superior to that of Silicalite-1 (pure silica ZSM-5), which is known to be good solid acid catalyst for the Beckmann rearrangement of cyclohexanone oxime up to date.

The present invention is illustrated in details, by the following Examples. However, it should be understood that the present invention is by no means restricted to the specific Examples.

MODES FOR CARRYING OUT THE INVENTION

PREPARATION EXAMPLE 1

A layered silicate, ilerite was synthesized hydrothermally in the laboratory using the following method. 2.1 g of sodium hydroxide (97 w %) was dissolved in 8.6 g of water in Teflon reaction vessel. 15 g of colloidal silica (Ludox-HS40®) was added to the above solution and stirred for 12 hours. After placing the Teflon reaction vessel in a stainless steel container, it was heated at 100° C. for 10 days. The product was filtered off, washed thoroughly with distilled water and dried in oven at 100° C.

PREPARATION EXAMPLE 2

Another layered silicate, magadiite was synthesized hydrothermally in the laboratory using the following method. 4.8 g of sodium hyroxide (97 w %) was dissolved in 105 g of water in a Teflon reaction vessel. 45 g of colloidal silica (Ludox-HS40®) was added to the above solution and stirred for 12 hours. After placing the Teflon reaction vessel in a stainless steel container, it was heated at 175° C. for one day. The product was filtered off, washed thoroughly with distilled water and dried in oven at 100° C.

EXAMPLE 1

Catalyst A was prepared from ilerite ($Na_2Si_8O_{17}xH_2O$) by the following method. First, the $Na^+$ ions between the ilerite layers were exchanged with $H^+$ ions by titraiting with 0.1 N hydrochloric acid to pH=2 and then stirred for 24 hours. The ilerite (H-ilerite) was washed thoroughly with distilled water and dried at 100° C. in oven. To expand the interlayer distance, 40 g of octylamine was added to 5 g of the H-ilerite. As octylamine added, the H-ilerite absorbed the amine and a gelatinous mixture was formed. The gel was used without further treatment for next step. 2.5 g of $Ta(OC_2H_5)_5$ was added to the gel and stirred for 48 hours at room temperature. The product was washed several times with ethanol, filtered off, and dried. Then, the resultant product was calcinated at 700° C. in air for 1 hour to remove amines. The chemical analysis showed that the amount of tantalum was 5 wt % in the catalyst. The surface area of Catalyst A was determined by a BET method and was determined to be 172 m²/g. Temperature-programmed desorption (TPD) of amimonia exhibits a broad desorption peak with maximum at 220° C. under 10° C. per minute of the heating rate. This implies that Catalysts A contains a large-number of acid sites having weak acidity.

EXAMPLE 2

Catalyst B was prepared from ilerite by the following method. 2.5 g of $Nb(OC_2H_5)_5$ was added to 45 g of H-ilerite-octylamine gel and stirred for 48 hours at room temperature. The product was washed several times with ethanol, filtered off, and dried. The resultant product was calcinated at 700° C. in air for 1 hour. The chemical analysis of Catalyst B showed that the amount of niobium was 4.8 wt %. The surface area of Catalyst B was determined by the BET method and was 168 m²/g. Also, a large and broad peak around 220° C. from ammonia TPD data indicated that the Catalyst B has a large amount of acid sites having weak acidity.

EXAMPLE 3

Catalyst C was prepared from ilerite by the following method. 1.0 g of $Ti(OC_2H_5)_5$ was added to 45 g of H-ilerite-octylamine gel and stirred for 48 hours at room temperature. The product was washed several times with ethanol, filtered off, and dried. The resultant product was calcinated at 700° C. in air for 1 hour. The surface area of Catalyst C was determined by BET method and was 164 m²/g.

EXAMPLE 4

Catalyst D was prepared from ilerite by the following method. 18.5 g of $Si(OC_2H_5)_5$ and 9.3 g of octylamine were mix. The mixture was added to 40 g of H-ilerite-octylamine gel and stirred for 48 hours at room temperature. Then, the product was washed several times with ethanol, filtered off and dried. The resultant product was calcinated at 700° C. in air for 1 hour. The surface area of Catalyst D was determined by the BET method and was 144 $m^2/g$.

EXAMPLE 5

Catalyst E was prepared-by pillaring $Ta_2O_5$ oligomers between the ilerite layers. After mixing and stirring 2.5 g of $Ta(OC_2H_5)_5$ and 1.0 g of octylamine for a few minutes at 50° C., 1.33 g of water was added to the mixture and stirred for 12 hours at room temperature to form $Ta_2O_5$ oligomers. After homogeneously mixing 2.5 g of $Ta_2O_5$ oligomer with 45 g of H-ilerite-octylamine gel in Teflon reaction vessel, the vessel was placed in a stainless- steel container. The obtained solid product was washed thoroughly with distilled water, dried at 100° C. in an oven and calcinated in air at 700° C. for 1 hour. The surface area of Catalyst E was determined by the BET method and was 367.4 $m^2/g$. X-ray powder diffraction data indicated that Catalyst E has interlayer distance in the range of 22 Å.

EXAMPLE 6

Catalyst F was prepared by pillaring $Nb_2O_5$ oligomers between the ilerite layers. After mixing and stirring 2.5 g of $Nb(OC_2H_5)_5$ and 1.0 g of octylamine for a few minutes at 50° C., 1.33 g of water was added to the mixture and stirred for 12 hours at room temperature to form $Nb_2O_5$ oligomers. After homogeneously mixing 2.5 g of $Nb_2O_5$ oligomer prepared as above with 45 g of H-ilerite-octylamine gel homogeneously in Teflon reaction vessel, the vessel was inserted in a stainless steel container and heated at 100° C. for 3 days. The obtained solid product was washed thoroughly with distilled water, dried at 100° C. in an oven and calcinated in air at 700° C. for 1 hour. The surface area of Catalyst F was determined by the BET method and was 395 $m^2/g$. X-ray powder diffraction data indicated that Catalyst E has interlayer distance in the range of 27 Å.

EXAMPLE 7

Catalyst G was prepared from magadiite ($Na_2Si_{14}O_{29}11H_2O$) prepared in Preparation Example 2 by the following method. First, the $Na^+$ ions between the magadiite layers was exchanged with $H^+$ ions by titrating with 0.1 N hydrochloric acid to pH 2 and stirred for 24 hours to obtain H-magadiite. This H-magadiite was washed thoroughly with distilled water and dried at 100° C. in an oven. 40 g of octylamine was added to 5 g of H-magadiite to form H-magadiite-octylamine gel. After stirring the gel for 12 hours at room temperature, the product was washed several times with ethanol, filtered off and dried. The solid product was calcinated in air at 700° C. for 1 hour to remove amines. The surface area of Catalyst G was determined by the BET method and was 280 $m^2/g$. X-ray powder diffraction data indicated that the interlayer distance of Catalyst G was is 13.5 Å.

EXAMPLES 8–14

Beckmann Rearrangement Reaction of Cyclohexanone Oxime

A Beckmann rearrangement reaction of cyclohexanone oxime was carried out in the presence of the catalysts prepared in Examples 1–7. The catalyst (0.3 g) was filled in a quartz reaction tube with inner diameter of 8 mm, and pretreated for 3 hours at 500° C. under helium gas. After the pretreatment, the reaction temperature was lowered to 350° C. A cyclohexnone oxime solution (mole ratio of ethanol/cyclohexanone oxime=9) was feeded to the reaction tube at 0.5 $hr^{-1}$ of raw material feed rate. The reaction product was collected hourly and analyzed by gas chromatography. The results of the reaction are listed in Table 1. In the Table, WHSV, conversion of cyclohexanone oxime and selectivity of caprolactam was calculated by the following formulas.

$$WHSV\ (1/hr) = \frac{Supply\ rate\ of\ cyclohexanone\ oxime\ (kg/hr)}{Total\ catalyst\ weight\ (kg)}$$

$$Conversion(\%)=((X-Y)/X)\times 100$$

$$Selectivity(\%)=(Z/(X-Y))\times 100$$

wherein, X=supplied cyclohexanone oxime (mol)
Y=unreacted cyclohexanone oxime (mol)
and Z=produced caprolactam (mol).

TABLE 1

| | Catalyst | Reaction time (h) | Conversion (%) | Selectivity (%) |
|---|---|---|---|---|
| Example 8 | A | 2 | 98.9 | 96.7 |
| | | 8 | 97.6 | 96.4 |
| Example 9 | B | 2 | 98.4 | 92.3 |
| | | 8 | 96.0 | 95.1 |
| Example 10 | C | 2 | 77.0 | 86.0 |
| | | 8 | 60.5 | 78.9 |
| Example 11 | D | 2 | 70.4 | 80.6 |
| | | 8 | 30.5 | 54.2 |
| Example 12 | E | 2 | 97.1 | 89.1 |
| | | 8 | 96.9 | 85.7 |
| Example 13 | F | 2 | 98.6 | 87.8 |
| | | 8 | 92.4 | 82.4 |
| Example 14 | G | 2 | 86.7 | 85.3 |
| | | 8 | 78.2 | 76.5 |

EXAMPLE 15–16

A Beckmann rearrangement reaction of cyclohexanone oxime was carried out in the presence of the catalysts prepared in Examples 1 and 2. The reaction condition was identical to that of examples 8–14 except that the cyclohexanone oxime solution was feeded at the WHSV 2.5 $hr^{-1}$. The results of the reaction are listed in Table 2.

TABLE 2

| | Catalyst | Reaction time (h) | Conversion (%) | Selectivity (%) |
|---|---|---|---|---|
| Example 15 | A | 2 | 99.1 | 95.6 |
| | | 8 | 97.5 | 87.4 |
| Example 16 | B | 2 | 99.0 | 94.8 |
| | | 8 | 96.4 | 85.5 |

The present invention provides a porous catalyst comprising layered silicate and metal oxide, and the preparation method thereof. The present invention also provides a method for preparing e-caprolactam from cyclohexanone oxime using the calyst of the present invention. This new catalyst is environmentally friendly and safe, and does not form wasteful by-products. Also the new catalyst solves the problem of short lifetime of the conventional solid acid catalysts. Moreover, the new catalyst provides high selectivity and conversion.

What is claimed:

1. A porous catalyst for preparing ε-caprolactam from cyclohexanone oxime in vapor phase, comprising layered silicate and metal oxides pillared between the silicate layers, wherein an interlayer distance between the silicate layers is in the range of 5 to 30 Å, and a surface area of the catalyst is in the range of 100 to 500 m²/g.

2. A porous catalyst according to claim 1, wherein the metal oxide is selected from the group consisting of tantalum oxide (Ta2O5), niobium oxide (Nb2O5), titanium oxide (TiO2) and silicon oxide (SiO2).

3. A porous catalyst according to claim 1, wherein the layered silicate is selected from the group consisting of kanemite, magadiite, kenyaite, makatite, ilerite and octosilicate.

4. A porous catalyst according to claim 1, wherein an amount of pillared metal oxide is in the range of 0.5 to 30% by weight of the catalyst.

5. A method for preparing a porous catalyst according to claim 1, comprising the steps: substituting Na+ of the layered silicate with H+ ion in an inorganic acid solution; extending interlayer distance between the silicate layers to 20–30 by using long chain amine; inserting metal oxide between the silica layers; and calcinating the resultant product.

6. A method for preparing ε-caprolactam by subjecting cyclohexanone oxime to a Beckmann rearrangement reaction in the presence of the catalyst according to claim 1 at temperature of 250 to 400 C at the WHVS of 0.1 to 10 hr−1 in a vapor phase.

7. A method for preparing a porous catalyst according to claim 2, comprising the steps: substituting Na+ of the layered silicate with H+ ion in an inorganic acid solution; extending interlayer distance between the silicate layers to 20–30 by using long chain amine; inserting metal oxide between the silica layers; and calcinating the resultant product.

8. A method for preparing a porous catalyst according to claim 3, comprising the steps: substituting Na+ of the layered silicate with H+ ion in an inorganic acid solution; extending interlayer distance between the silicate layers to 20–30 by using long chain amine; inserting metal oxide between the silica layers; and calcinating the resultant product.

9. A method for preparing a porous catalyst according to claim 4, comprising the steps: substituting Na+ of the layered silicate with H+ ion in an inorganic acid solution; extending interlayer distance between the silicate layers to 20–30 by using long chain amine; inserting metal oxide between the silica layers; and calcinating the resultant product.

10. A method for preparing ε-caprolactam by subjecting cyclohexanone oxime to a Beckmann rearrangement reaction in the presence of the catalyst according to claim 2 at temperature of 250 to 400 C at the WHVS of 0.1 to 10 hr−1 in a vapor phase.

11. A method for preparing ε-caprolactam by subjecting cyclohexanone oxime to a Beckmann rearrangement reaction in the presence of the catalyst according to claim 3 at temperature of 250 to 400 C at the WHVS of 0.1 to 10 hr−1 in a vapor phase.

12. A method for preparing ε-caprolactam by subjecting cyclohexanone oxime to a Beckmann rearrangement reaction in the presence of the catalyst according to claim 4 at temperature of 250 to 400 C at the WHVS of 0.1 to 10 hr−1 in a vapor phase.

* * * * *